United States Patent
Kuiper et al.

(10) Patent No.: US 10,743,759 B2
(45) Date of Patent: Aug. 18, 2020

(54) OPTICAL COHERENCE TOMOGRAPHY METHOD, SYSTEM AND COMPUTER PROGRAM PRODUCT THEREFOR

(71) Applicant: Nederlandse Organisatie voor toegepast-natuurwetenschappelijk onderzoek TNO, 's-Gravenhage (NL)

(72) Inventors: Stefan Kuiper, 's-Gravenhage (NL); Nicolaas Jan Doelman, 's-Gravenhage (NL); Thomas Liebig, 's-Gravenhage (NL); Willem Arjan Klop, 's-Gravenhage (NL)

(73) Assignee: NEDERLANDSE ORGANISATIE VOOR TOEGEPAST-NATUURWETENSCHAPPELIJK ONDERZOEK TNO, 's-Gravenhage (NL)

( * ) Notice: Subject to any disclaimer, the term of this patent is extended or adjusted under 35 U.S.C. 154(b) by 3 days.

(21) Appl. No.: 15/559,266

(22) PCT Filed: Mar. 17, 2016

(86) PCT No.: PCT/NL2016/050186
§ 371 (c)(1),
(2) Date: Sep. 18, 2017

(87) PCT Pub. No.: WO2016/148569
PCT Pub. Date: Sep. 22, 2016

(65) Prior Publication Data
US 2018/0092527 A1 Apr. 5, 2018

(30) Foreign Application Priority Data
Mar. 19, 2015 (EP) ..................... 15159891

(51) Int. Cl.
*A61B 3/10* (2006.01)
*A61B 3/15* (2006.01)
(Continued)

(52) U.S. Cl.
CPC ............ *A61B 3/102* (2013.01); *A61B 3/1225* (2013.01); *A61B 3/14* (2013.01); *A61B 3/15* (2013.01);
(Continued)

(58) Field of Classification Search
CPC ......... A61B 3/102; A61B 3/1225; A61B 3/14; A61B 3/15; G06T 1/0007; G06T 5/50; G01B 9/02091
See application file for complete search history.

(56) References Cited

U.S. PATENT DOCUMENTS 5,094,523 A 3/1992 Reznichenko et al.
6,325,512 B1 12/2001 Wei
(Continued)

FOREIGN PATENT DOCUMENTS

JP 2014176442 A 9/2014
WO 2015010133 A1 1/2015

*Primary Examiner* — Menatoallah Youssef
(74) *Attorney, Agent, or Firm* — Hoffmann & Baron, LLP

(57) ABSTRACT

The present invention relates to an optical coherence tomography method, comprising: providing a beam of imaging radiation from a radiation source of an optical coherence tomography apparatus; directing, using directing optics, the beam of imaging radiation towards a fundus of a human or animal eye; and receiving a reflected portion of the imaging radiation by the optical coherence tomography apparatus; wherein the method further comprises: providing, by a tracking camera, a tracking image of an image area covering at least a part of said fundus; analyzing the tracking image for detecting a displacement of the fundus; and adapting, at least dependent on the detected displacement, a direction of the beam of imaging radiation by actuating an optical (Continued)

correction unit of said direction optics; and in addition to said adapting of the direction of the beam of imaging radiation, adapting a location of the image area on said fundus imaged by the tracking camera at least dependent on the detected displacement.

20 Claims, 6 Drawing Sheets

(51) Int. Cl.
*A61B 3/12* (2006.01)
*A61B 3/14* (2006.01)
*G01B 9/02* (2006.01)
*G06T 1/00* (2006.01)
*G06T 5/50* (2006.01)

(52) U.S. Cl.
CPC ........ *G01B 9/02091* (2013.01); *G06T 1/0007* (2013.01); *G06T 5/50* (2013.01)

(56) References Cited

U.S. PATENT DOCUMENTS

| | | |
|---|---|---|
| 2007/0252951 A1 | 11/2007 | Hammer et al. |
| 2012/0274783 A1 | 11/2012 | Ko et al. |
| 2014/0226130 A1* | 8/2014 | Everett ................. A61B 3/102 351/210 |
| 2014/0334707 A1 | 11/2014 | Teiwes et al. |
| 2015/0131050 A1* | 5/2015 | Bublitz ................ A61B 3/1025 351/206 |

* cited by examiner

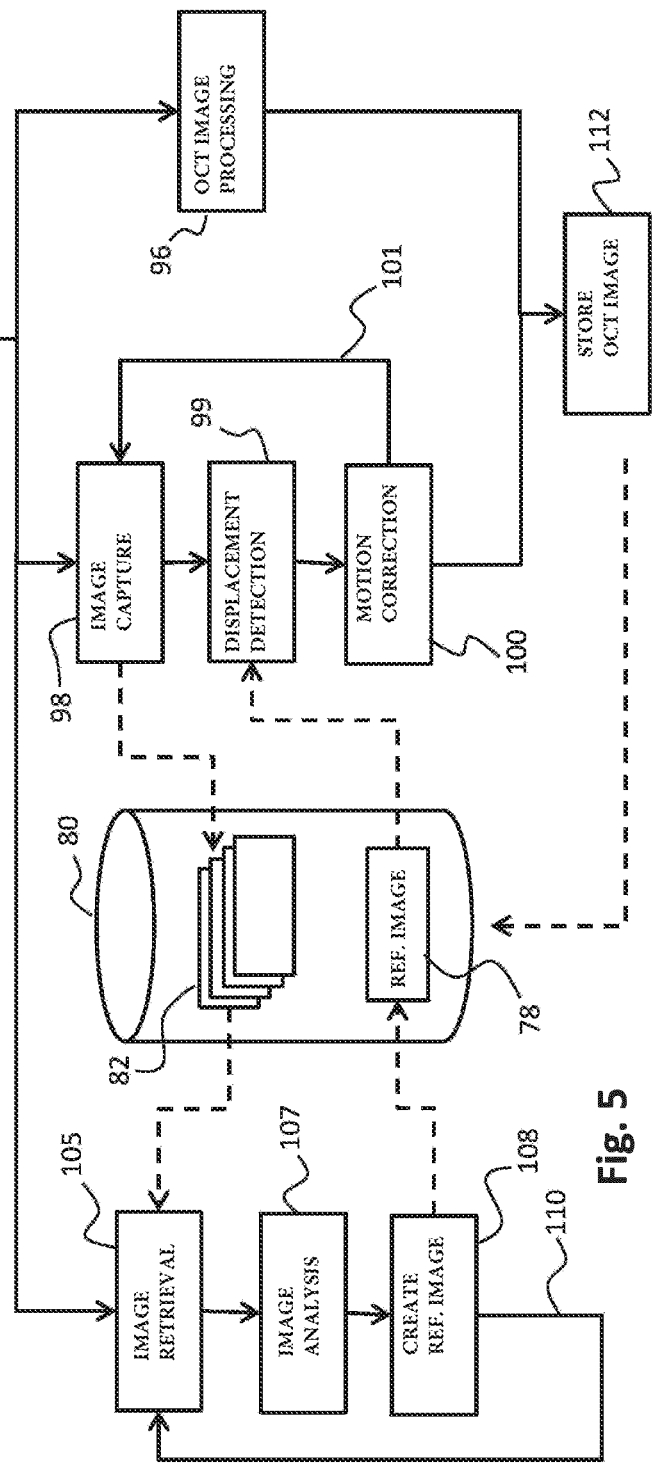
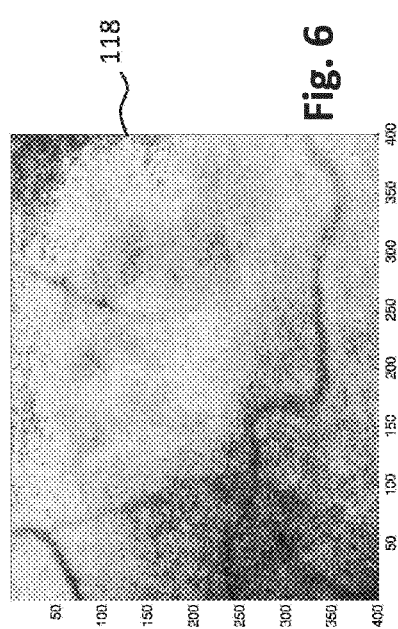
Fig. 6
Fig. 5

OPTICAL COHERENCE TOMOGRAPHY METHOD, SYSTEM AND COMPUTER PROGRAM PRODUCT THEREFOR

This application is the U.S. National Phase of, and Applicant claims priority from, International Patent Application Number PCT/NL2016/050186 filed 17 Mar. 2016, which claims priority from EP 15159891.9 filed 19 Mar. 2015, each of which is incorporated herein by reference.

FIELD OF THE INVENTION

The present invention is directed at an optical coherence tomography method, comprising providing a beam of imaging radiation from a radiation source of an optical coherence tomography apparatus; directing, using directing optics, the beam of imaging radiation towards a fundus of a human or animal eye; and receiving a reflected portion of the imaging radiation by the optical coherence tomography apparatus.

The invention is further directed at an optical coherence tomography system, comprising an optical coherence tomography apparatus including a radiation source for providing a beam of imaging radiation, an optical receiver for receiving a reflected portion of the imaging radiation, and an analysis unit for analyzing the received reflected portion of the imaging radiation. The invention is further directed at a computer readable medium comprising computer program product.

BACKGROUND

Optical retinal imaging is class of a medical imaging techniques that is applied in medical diagnosis and treatment methods to examine the fundus of an eye. A number of these methods is based on the scanning of a beam of imaging radiation across the fundus. The scanning is performed step-by-step, and image data for a pixel (or for a line of pixels) is obtained from reflected radiation during each scanning step. These optical retinal imaging techniques for example include optical coherence tomography (OCT), confocal scanning laser ophthalmology (cSLO), and line scanning laser ophthalmology (lSLO).

Optical coherence tomography (OCT), for example, is a medical imaging technique that is based on interferometry using a reflected portion of light penetrating into biological tissue. OCT is for example applied in ophthalmology to obtain detailed images of sub-surficial and surficial structures on and below the retina of an eye. In this field, OCT has become a well established method of diagnosing many eye diseases.

In OCT, a beam of imaging radiation is impinged on for example the fundus of an eye and the reflected part is led through an interferometer wherein it interferes with a reference beam. By scanning the imaging radiation across an area of the fundus, a (three dimensional) image may be obtained from the interference pattern. Although OCT has the potential to enable ophthalmologic imaging at high resolution, at present the lateral resolution is strongly limited by eye motions of the eye under examination. These motions may be divided in three different types, including eye tremor, drift and micro saccades. The first one—tremor—may be characterized as a vibrating motion of the eye having a typical frequency around 90 Hz and a typical amplitude of approximately 1 µm. The second type of motion may cause the eye to move across a distance of for example 0.1 mm but at a typical frequency of 1 Hz. The micro saccades may also have a typical period of 1 Hz, with a duration of only 25 ms typically and an amplitude of 25-100 µm. The peak velocity of these micro saccades may be 10 mm/sec.

Adaptive Optics OCT systems presently under development, will enable to reduce the ocular resolution of the system down to approximately 3 µm (micrometer). To enable measurement at this resolution, residual eye motion must somehow be controlled or compensated such that the error introduced is typically below 1 µm (micrometer).

To improve accuracy, OCT systems and other retinal imaging systems for ophthalmologic purposes sometimes cooperate with tracking devices or tracker camera's. The tracker camera may for example include a fundus camera which generates a reference image from which any eye movements can be detected and analyzed. Additional correction optics may then correct the imaging beam to impinge on the correct location on the fundus. The taking of the reference image and the correcting of the beam is usually performed after each scanning step correct for any eye motion occurring during scanning. However, the present tracking devices are still not accurate enough to compensate for eye motion sufficiently, to obtain the required accuracy for correcting the optical retinal imaging system.

SUMMARY OF THE INVENTION

In view of the above, it is an object of the present invention to provide an OCT method and system that allows highly accurate correction of the imaging beam.

To this end, there is provided herewith an optical retinal imaging method, comprising: providing a beam of imaging radiation from a radiation source of an optical retinal imaging apparatus; directing, using directing optics, the beam of imaging radiation towards a fundus of a human or animal eye; and receiving a reflected portion of the imaging radiation by the optical retinal imaging apparatus; wherein the method further comprises: providing, by a tracking camera, a tracking image of an image area covering at least a part of said fundus; analyzing the tracking image for detecting a displacement of the fundus; and adapting, at least dependent on the detected displacement, a direction of the beam of imaging radiation by actuating an optical correction unit of said direction optics; and in addition to said adapting of the direction of the beam of imaging radiation, adapting a location of the image area on said fundus imaged by the tracking camera at least dependent on the detected displacement.

In accordance with the present invention, a displacement detected using the tracking image of the tracking camera is used to adapt the direction of the beam of imaging radiation, and in addition this information is also used to adapt the location of the image area of the tracking image. For example, the viewing direction of the tracking camera may be adapted using a feedback system, based on the displacement detected by comparison of the last or one or more of the last tracking images with one or more earlier tracking images.

In particular, the tracking image obtained by the tracking camera is analyzed and may be compared to earlier images to detect a relative displacement of one or more image features in the image. These image features may for example include features that are visible on the fundus of the eye, such as the macula, the optic disc or a blood vessel or other image feature visible. Preferably, the image feature is visible in the tracking image with sufficient contrast to enable accurate detection of a displacement. However, even in case the contrast of a feature may be limited, image analysis algorithms may be applied to improve the detection of a displacement as will be appreciated by the skilled person.

Assuming that the camera position and orientation are fixed and do not change from image to image, when a displacement is detected it can be assumed that the displacement is caused by motion of the eye. Such a displacement may thus be the result of micro saccades, drift or tremor. Given the amplitude and involved displacement velocities, motion caused by micro saccades may have major impact on the accuracy of the OCT system. In particular, in case an allowed displacement error of only 1.0 μm (micrometers) is to be achieved, a displacement velocity of typically 10 mm/sec (millimeters per second) could in 0.01 seconds (e.g. between two consecutive images taken at 100 Hz) result in a displacement over 100 μm (micrometers). Because micro saccades of the eye typically move over a distance of 25 to 100 μm (micrometer), the maximum inaccuracy caused by micro saccades may also approximately be equal to this distance. The influence of drift is smaller due to the much lower velocity, although the overall displacement distance can be larger. From the tracking image, the displacement is detected and the direction of the OCT imaging radiation beam is adapted to correct for the inaccuracy. In addition, in accordance with the invention, also the image area imaged by the tracking camera is adapted based on the detected displacement, such that the image area for the tracking image is corrected for the displacement. Ideally, the image area is completely corrected for the displacement, such that the corrected image area is again the same image area as before the displacement. However, it is not a strict requirement to completely correct the tracking image for the displacement as long as the displacement is corrected sufficiently to yield a largely overlapping set of tracking images.

The present invention is based on the insight that a sufficient overlap between the successive images of the tracking camera is needed to allow reliable tracking. In the present invention, this is achieved by correcting the image area of the tracking image in addition to correction of the direction of the OCT imaging beam based on eye movements. As a result, the image area on the fundus of the eye will remain more or less the same in subsequent images and is corrected as soon as a displacement is detected. The subsequent tracking images will thus have a large overlap. This enables to reduce the image area to an optimal size— that is, a size that provides sufficient information to reliably determine displacements while at the same time being small enough to enable fast processing. The smaller size of the tracking image (as compared to conventional tracking) enables faster processing times of the images of the tracking camera. This faster processing time can be used to increase the number of images taken per unit of time, i.e. the imaging rate, which in turn provides more accuracy as the displacement distance will be shorter between two consecutive images in case the time passed in between these images decreases.

As already referred to above, preferably for allowing OCT imaging the beam of imaging radiation is scanned across an examination area on the fundus. By scanning the beam across the examination area, the reflected portion of the imaging radiation can be analyzed by the OCT system to provide a (three dimensional) image of the examination area from an interference pattern. The three dimensional image visualizes the fundus surface, and the structure of the tissue below the surface, to a typical penetration depth of several millimeters. The interference pattern is obtained using an interferometer by interfering the reflected portion with a reference beam. For example, the reference beam may be taken from the same radiation source as the beam of imaging radiation, but having a fixed optical path length and thus known or at least fixed phase and identical optical properties as the beam of imaging radiation. Please note that throughout this document the term 'examination area' is used in order to refer to the area imaged by the OCT imaging radiation beam. This is to prevent confusion with the term 'image area' used in this document to refer to the tracking image provided by the tracking camera.

In accordance with an embodiment of the present invention, said adapting of the location of the image area on the fundus is achieved by disposing the tracking camera such as to receive an optical tracking signal of said image area by the tracking camera via the optical correction unit. An important advantage of this embodiment that once the OCT system and the tracking camera are correctly set up, operating the optical correction unit allows at the same time to perform both: the adapting of the direction of the beam of imaging radiation, as well as the adapting of the location on the fundus of the image area of the tracking camera. To this end, the set up includes disposing the radiation source of the OCT system such that the beam of imaging radiation reaches the surface of the fundus having the optical correction unit in its optical path. Additionally, the set up includes disposing the tracing camera such that it allows capturing of the tracking images of the image area from an optical signal received via an optical path that at least includes the correction unit.

In addition to the above, because the optical correction unit corrects both the location of the image area of the tracking image as well as the direction of the beam of imaging radiation (and thereby also the examination area), the relative locations of the image area and the examination area with respect to each other will not change when the optical correction unit is operated. There is no requirement with respect to the size of the image area in relation to that of the examination area. For the image area, from analysis of subsequent tracking images it must be possible to detect the displacement of the eye by eye motion. The size of the examination area is chosen to allow examination of a specific area usually for medical purposes. Therefore, the examination area may often include a specific area containing a feature to be examined, which may be larger than, smaller than, or comparable to the image area. The image area is of a size such that the overlap between two subsequent tracking images obtained during an eye movement (or before and after an eye movement) contains sufficient overlap to allow detection of the displacement with sufficient accuracy. As may be appreciated, the accuracy may improve in case the tracking images comprises multiple image features from which the displacement can be detected. However, at the same time, increasing the size of the tracking image strongly increases the duration of the detection because more data needs to be analyzed. An optimum is found if the overlap between two subsequent images is just enough to allow detection of the displacement with sufficient accuracy to perform the adapting of the direction of the beam of imaging radiation by the optical correction unit. Hence, this allows to reduce the size of tracking images to this optimum.

In accordance with another embodiment of the present invention, the step of providing the tracking image in the optical retinal imaging method is formed subsequently to provide a plurality of subsequent tracking images during said providing of the beam of imaging radiation, the method further including a step of providing a reference tracking image, wherein the reference tracking image is obtained using an exposure time longer than an exposure time use for the subsequent tracking images. In accordance with this embodiment, in fact a reference tracking image is obtained with a long exposure time such as to provide the reference tracking image with a higher illumination power than the subsequent images. The longer exposure time of the reference tracking image improves the signal-to-noise ratio (SNR) of the image. The increased SNR of the reference tracking image obtained makes image correlation between subsequent tracking images more robust against noise and therefore allowing shorter exposure times for the subsequent tracking images.

Using the reference image, the detection of displacements of the fundus becomes more reliable as a result of the higher SNR. This is utilized to improve the correlation between subsequent tracking images, and therefore the exposure time of the subsequent tracking images may be shortened while maintaining the reliability of the results at least at the same level. The shorter exposure time can be used to increase the imaging rate (the number of images per second) of the tracking camera. By increasing the imaging rate, the displacement between subsequent tracking images likewise becomes smaller while the accuracy of correcting the direction of the beam of imaging radiation improves. This enables to further reduce the residual eye motion between subsequent tracking images improving the accuracy of the system.

The reference tracking image may be obtained in various ways. In accordance with one embodiment, the reference tracking image is obtained separately, as a separate step performed prior to the steps of subsequently providing the subsequent tracking images. In this embodiment, the reference tracking image is captured first with a long enough exposure time. For example the exposure times for the reference image may be up to 20 milliseconds, although it is advisable not to expose longer than 10 milliseconds using a high illumination power (e.g. using a flash). The reference tracking images will be obtained prior to the OCT imaging (scanning the surface of the fundus with the beam of imaging radiation of the OCT system).

In yet another embodiment, obtaining the reference tracking image may be performed by combining image data from two or more of the subsequent tracking images such as to establish the longer exposure time of the reference tracking image. In this latter embodiment, the reference tracking image is obtained 'on the fly', by combining the overlapping parts of the subsequent tracking images. As will be appreciated, each tracking image is obtained using a given exposure time, and by combining the overlapping parts of subsequent tracking images, an image of this overlapping part is obtained with an exposure time which is the sum of the exposure times of the combined subsequent tracking images. As will be appreciated obtaining the reference tracking images in this matter 'on the fly' overcomes the need of having to obtain the reference tracking image as a separate step prior to the OCT imaging of the examination area. Moreover, while the number of tracking images increases during tracking, the quality of the reference image can be constantly improved during tracking. The requirements for safe illumination of the fundus during continuous or prolonged exposure are more stringent than for taking a single reference image up front. For example, the radiation power of the OCT beam—a collimated beam—is preferably smaller than or equal to 600 microwatt. For the subsequent tracking images, the illumination power from the non-collimated illumination source may be higher (for example 1 milliwatt). The maximum allowed illumination power for a flash, such as may be applied for obtaining an up-front reference image as referred to in the above embodiment, are not strictly defined. However, it may be assumed here that an illumination power of 10 milliwatt is allowable, which will enable a good quality reference image to be taken.

In accordance with another embodiment of the present invention, a tracking image which is used in the optical retinal imaging method is obtained using a fundus camera.

The optical retinal imaging method may relate to or include any one or more of a group comprising an optical coherence tomography method, a confocal scanning laser ophthalmoscopy method, or a line scanning laser ophthalmoscopy method. These retinal imaging methods all have in common that an image is formed by subsequently obtaining image data from a reflected fraction of a beam that is scanned pixel-by-pixel or line-by-line across the fundus to be examined. For example in optical coherence tomography, image data for each pixel of the image is obtained by illuminating the corresponding origin of that pixel on the fundus during a single scanning step. By scanning the surface area to be imaged step-by-step, the image can be built pixel-by-pixel. A tracking image of a tracking camera may be analyzed in between each two subsequent scanning steps for performing said adapting of the direction of the beam of imaging radiation and the location of the image area of the tracking image between these steps. In another example, wherein the retinal imaging method is a line scanning laser ophthalmoscopy method, same is done line-by-line, i.e. a flat, line-shaped beam is scanned step-by-step across the surface area to be imaged, such as to obtain image data of all pixels included in the line-shaped beam at once.

In accordance with a further aspect of the present invention, there's provided an optical retinal imaging system, comprising an optical retinal imaging apparatus including a radiation source for providing a beam of imaging radiation, an optical receiver for receiving a reflected portion of the imaging radiation, and an analysis unit for analyzing the received reflected portion of the imaging radiation; the system further comprising directing optics for directing the beam of imaging radiation towards a fundus of a human or animal eye, a tracking camera for providing a tracking image of an image area covering at least a part of said fundus, and a control unit for receiving and analyzing the tracking image for detecting a displacement of the fundus during irradiation thereof by the optical retinal imaging apparatus; wherein the directing optics include an optical correction unit operatively connected to the control unit for enabling adapting of a direction of the beam of imaging radiation at least dependent on the detected displacement, by actuation of the optical correction unit; and a camera image correction unit for adapting, in addition to said adapting of the direction of the beam of imaging radiation, a location of the image area on said fundus imaged by the tracking camera at least dependent on the detected displacement.

The camera image correction unit in the above described OCT system may be a separate correction unit in addition to the optical correction unit for correcting or adapting the direction of the beam of imaging radiation. However, in accordance with an embodiment, the camera image correction unit comprises the optical correction unit. In this embodiment, the direction of the beam of imaging radiation and the imaging signal received by the tracking camera of the location of the image area are corrected by one and the same unit: the optical correction unit. Advantages of this embodiment have been described hereinabove with reference to the first aspect.

In another embodiment of the present invention the optical correction unit comprises at least one mirror connected to an actuator for controlling at least one of the orientation or position of the mirror relative to the beam of imaging radiation for adapting the direction thereof. The actuator may for example include a galvanometer, which allows to adapt the direction of the beam of imaging radiation with a very high precision, as the skilled person may appreciate.

The OCT system in accordance with the present invention may further comprise a scanning unit for enabling scanning of the beam of imaging radiation across an examination area on the fundus.

In yet another embodiment, the control unit is arranged for receiving a plurality of subsequent tracking images during said providing of the beam of imaging radiation, wherein the control unit is further arranged for obtaining a reference tracking image, wherein the reference tracking image is obtained using an exposure time and/or illumination power longer than that used for the subsequent tracking images. The advantages of obtaining a reference tracking images having a longer exposure time and thereby increased signal-to-noise ratio (SNR) have been explained hereinabove. In a particular embodiment of the second aspect, the control unit is arranged for obtaining the reference tracking image by combining the image data from two or more of the subsequent tracking images such as to establish the longer exposure time of the reference tracking image. As explained, in this case the control unit may for example determine the area of overlap between the subsequent tracking images and combine the overlapping area into a reference tracking image having an exposure time which is the sum of the combined subsequent tracking images. As may be appreciated, to obtain the reference tracking image the control unit may combine any desired number of subsequent tracking images: the control unit may combine n subsequent tracking images wherein n>2 and n is a natural number (n=1, 2, 3, 4, 5, . . . ).

In some embodiments, the optical retinal imaging system comprises at least one of a group comprising: an optical coherence tomography system, a confocal scanning laser ophthalmoscopy system, or a line scanning laser ophthalmoscopy system.

In accordance with a third aspect of the present invention there is provided a computer readable medium comprising a computer program product comprising instructions that, when executed by a optical retinal imaging system causes the system to perform a method comprising controlling a radiation source of an optical retinal imaging apparatus comprised by the system to provide a beam of imaging radiation; and controlling directing optics to direct the beam of imaging radiation towards a fundus of a human or animal eye; and controlling the optical retinal imaging apparatus receive a reflected portion of the imaging radiation; the method further comprises controlling a tracking camera to provide a tracking image of an image area covering at least a part of said fundus; and obtaining and analyzing the tracking image by a control unit for detecting a displacement of the fundus; and adapting, at least dependent on the detected displacement, a direction of the beam of imaging radiation by actuating an optical correction unit of said direction optics; and in addition to said adapting of the direction of the beam of imaging radiation, adapting a location of the image area on said fundus imaged by the tracking camera at least dependent on the detected displacement.

BRIEF DESCRIPTION OF THE DRAWINGS

The invention will further be elucidated by description of some specific embodiments thereof, making reference to the attached drawings. The detailed description provides examples of possible implementations of the invention, but is not to be regarded as describing the only embodiments falling under the scope. The scope of the invention is defined in the claims, and the description is to be regarded as illustrative without being restrictive on the invention. In the drawings:

FIG. 5 illustrates a further method in accordance with the present invention;

FIG. 6 illustrates a reference image of a fundus;

DETAILED DESCRIPTION

Figure 1:
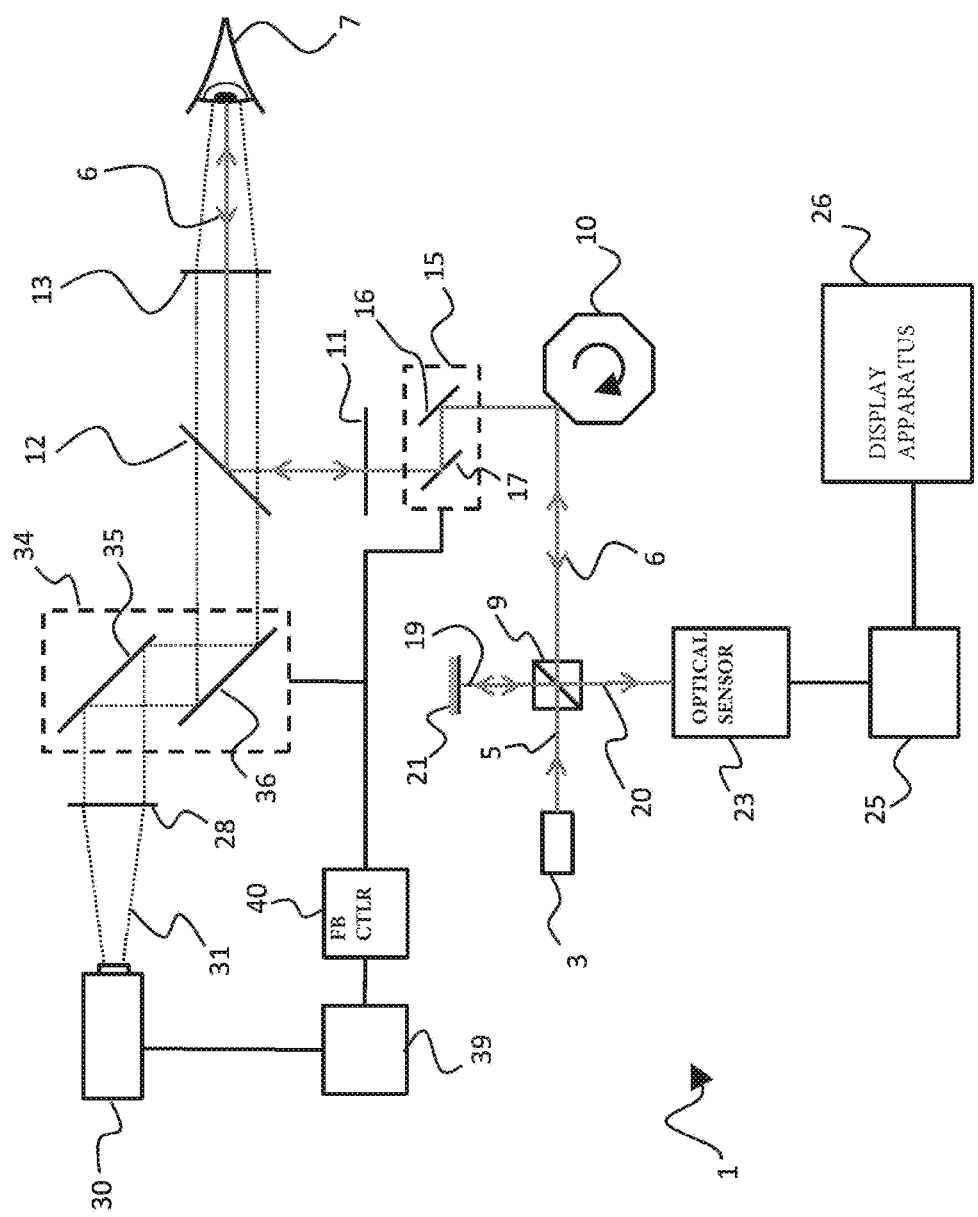
FIG. 1 schematically illustrates an optical coherent tomography system in accordance with an embodiment of the present invention.

In FIG. 1, an optical coherent tomography [OCT] system is generally indicated by reference numeral 1. The system includes a radiation source 3 providing a beam 5 of imaging radiation. The beam 5 is directed towards an eye 7 of a human or animal, which eye 7 is to be examined. In particular, the optical coherent tomography system 1 allows for example to examine the fundus of the eye 7.

The beam 5 of imaging radiation is directed towards the eye 7 by means of a number of optical elements (10, 11, 12, 13 and 15). The optical elements for directing the beam 5 of imaging radiation may include lenses 11 and 13 for correctly focusing of the radiation. The optical elements further include a mirror element 12 which comprises a specular reflective surface on one side, but which is transmissive on the other side such as to allow the camera 30 to have a field of view with the eye 7 (as will be explained later). The optical elements further includes scanning optics 10 comprising a rotatable polygon mirror 10. By rotating the mirror 10, a scanning motion of the beam 5 in the optical path between the mirror 10 and the eye 7 can be obtained. This scanning motion provided by polygon mirror 10 may be used to scan the beam 5 across an examination area on the fundus of the eye 7. The implementation of scanning based on a rotating polygon mirror is merely an example, and many other methods and units may be applied here to provide the scanning. Such units may generally be referred to as 'optical scanning units'.

A reflected portion 6 of the imaging radiation follows the same optical path from the fundus of the eye 7 back to the beam splitter 9. The beam splitter 9 forms the heart of a Michelson type interferometer. Although in FIGS. 1 and 2 a Michelson type interferometer is illustrated, the skilled person may appreciate that any other type of interferometer (such as a Mach-Zehnder interferometer (MZI)) may be applied as well. The invention is not limited to a specific type of interferometer. The reflected portion 6 of the beam 5 impinges on the beam splitter 9 and is directed towards leg 20 which impinges on optical sensor 23. The beam splitter 9 splits the beam 5 of imaging radiation obtained from radiation source 3 such as to create a reference beam 19 in addition to the remainder of the beam 5 which is directed towards the eye 7. The reference beam 19 is reflected upon a mirror 21 and part of the reflected radiation will be transmitted into leg 20 towards the optical sensor 23. The combined beam in leg 20, containing the reflected portion 6 of the beam 5 and the reference beam 19, creating an interference pattern that can be analyzed with optical sensor 23. From the interference pattern obtained, analysis unit 25 is able to create the OCT image, and provide the OCT image of the examination area of the fundus of eye 7 to the display apparatus 26. As may be appreciated, the image obtained may be stored in a memory or provided to a network server or other means.

As described hereinabove, because the OCT imaging method is performed on a living eye, eye movements will result in a undesired displacement of the impact location of the beam 5 on the fundus. This is because due to the eye movement, the fundus will move relatively to the beam 5. To resolve and correct for these undesired displacements, the OCT system comprises a tracking camera 30. The tracking camera 30 comprises a field of view 31 directed towards optical element 28 for focusing, and via half mirror 12 and optical element 13 to the fundus of the eye 7. Tracking may for example be a fundus camera which allows to recreate a detailed image of the fundus of the eye. The images obtained with tracking camera 30 are analyzed by analysis unit 39 and our provided to feedback controller 40 which controls optical correction unit 15. Optical correction unit 15 comprises galvanometer actuated mirrors 16 and 17 which allow to precisely correct the beam 5 in the x and y directions (i.e. the directions perpendicular to the optical axis). Using the optical correction unit 15, the direction of the beam 5 of imaging radiation can be adapted to correct for the displacements of the eye 7.

In accordance with the present invention, the feedback controller 40 further controls camera image correction unit 34 comprising galvanometer actuated mirrors 35 and 36 for adapting the direction of the field of view 31 of the tracking camera in the x and y direction. By simultaneously controlling camera image correction unit 34 and optical correction unit 15, a large overlap between the subsequent tracking images obtained with the tracking camera 30 can be achieved while simultaneously precisely correcting the direction of the beam 5 of imaging radiation for the eye movements. The advantage is two-fold. Firstly, the overlap between subsequent tracking images of the tracking camera 30 may be maximized by the correction. This allows the overall size of the images to be made smaller while maintaining the ability to accurately determine the displacements. Secondly, because the correction of the field of view of the tracking camera 30 as well as the correction of the direction of the beam 5 of imaging radiation of the OCT system are based on the same measured displacement, any relative movement between the examination area of the OCT imaging and the image area of the tracking camera will be down to a minimum (e.g. only due to inaccuracies or differences between the optical correction unit 15 or the camera image correction unit 34). This further allows to reduce the size of the tracking images. As a result, due to the reduced size of the tracking images obtained with the tracking camera 30, the analysis of subsequent tracking images to detect displacements of the fundus can be performed faster, thereby also allowing a higher imaging rate (number of images taken per second) of the tracking camera. Due to the higher imaging rate, displacements caused by eye motion result in smaller deviations between subsequent images, and the system is therefore better capable of following the eye movement and correcting for this. As a result, the accuracy and resolution of the OCT image can be improved.

Figure 2:
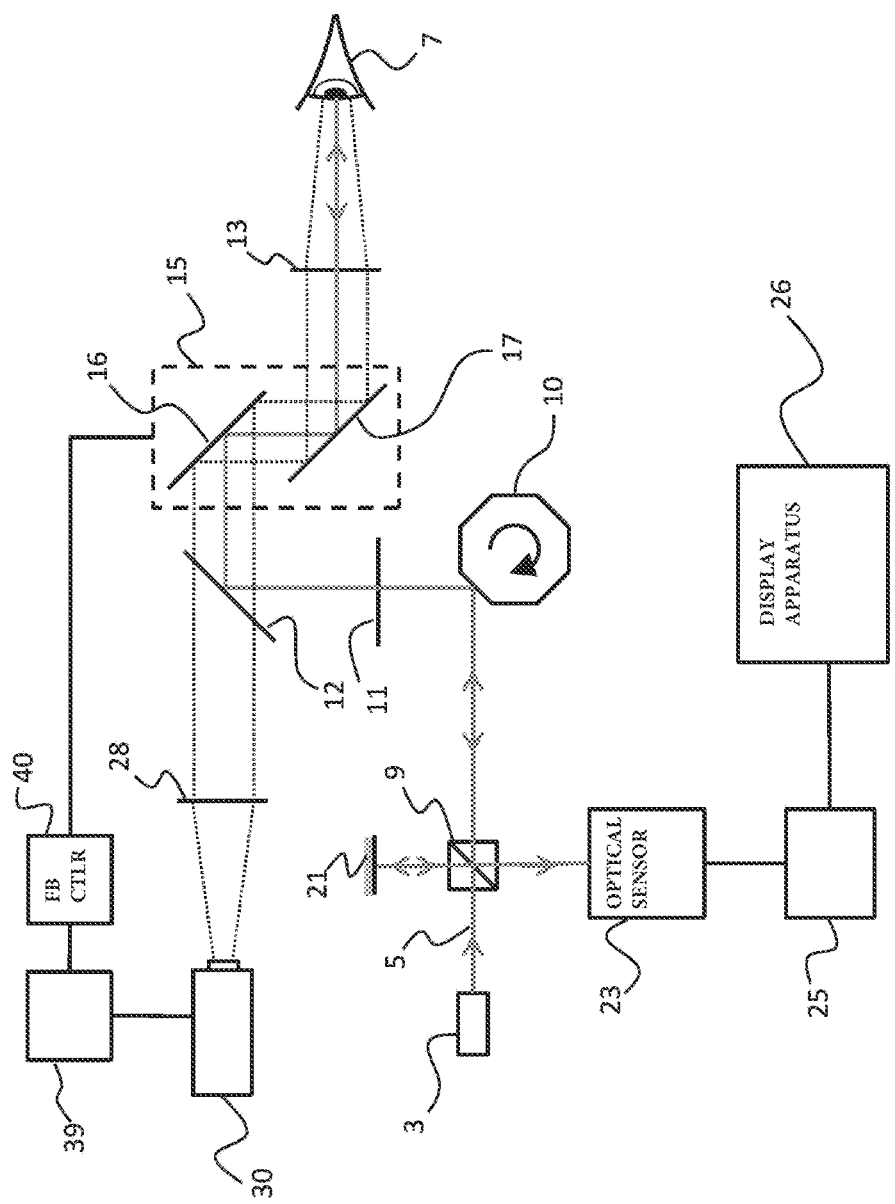
FIG. 2 schematically illustrates a further embodiment of the present invention.

A further embodiment of the present invention is illustrated in FIG. 2. In FIG. 2, elements performing a similar function for being identical to the embodiment illustrated in FIG. 1 have been indicated with the same reference numerals. Such elements are only further discussed hereinbelow where needed.

The main difference between the embodiment illustrated in FIG. 2 and that of FIG. 1 is that in the embodiment of FIG. 2, the optical correction unit 15 also performs the correction of the field of view of the tracking camera 30. In other words, the optical correction unit 15 and the camera image correction unit 34 of FIG. 1 have been integrated into a single element in the embodiment of FIG. 2. All corrections that are performed by the optical correction unit 15 on the beam 5 of imaging radiation of the OCT system are automatically also applied to the field of view 31 of tracking camera 30. As a result, the location of the examination area for OCT imaging will be fixed relative to the image area of the tracking image of tracking camera 30. As will be appreciated, for examining different parts of the fundus, the size and location of the examination area of the fundus of the eye 7 may differ from one image to the other obtained with the OCT system. However, due to the combined optical correction unit 15 with mirrors 16 and 17, the examination area of the OCT image may for example always recite in the middle of the tracking image (unless the location or orientation of the camera 30 itself may change).

The present embodiment illustrated in FIG. 2 provides several advantages. The overall system set up becomes less complex, and the whole OCT system illustrated in FIG. 2 comprises less elements. Moreover, by correcting the image area of the tracking images and the direction of the beam 5 using the same optical correction unit 15, any possible deviation between the location of the examination area and the image area as prevented. This allows the image area of the tracking image to be smaller, but most importantly, a further source of measurement errors caused by discrepancies between the image area and the examination area is excluded.

Figure 3:
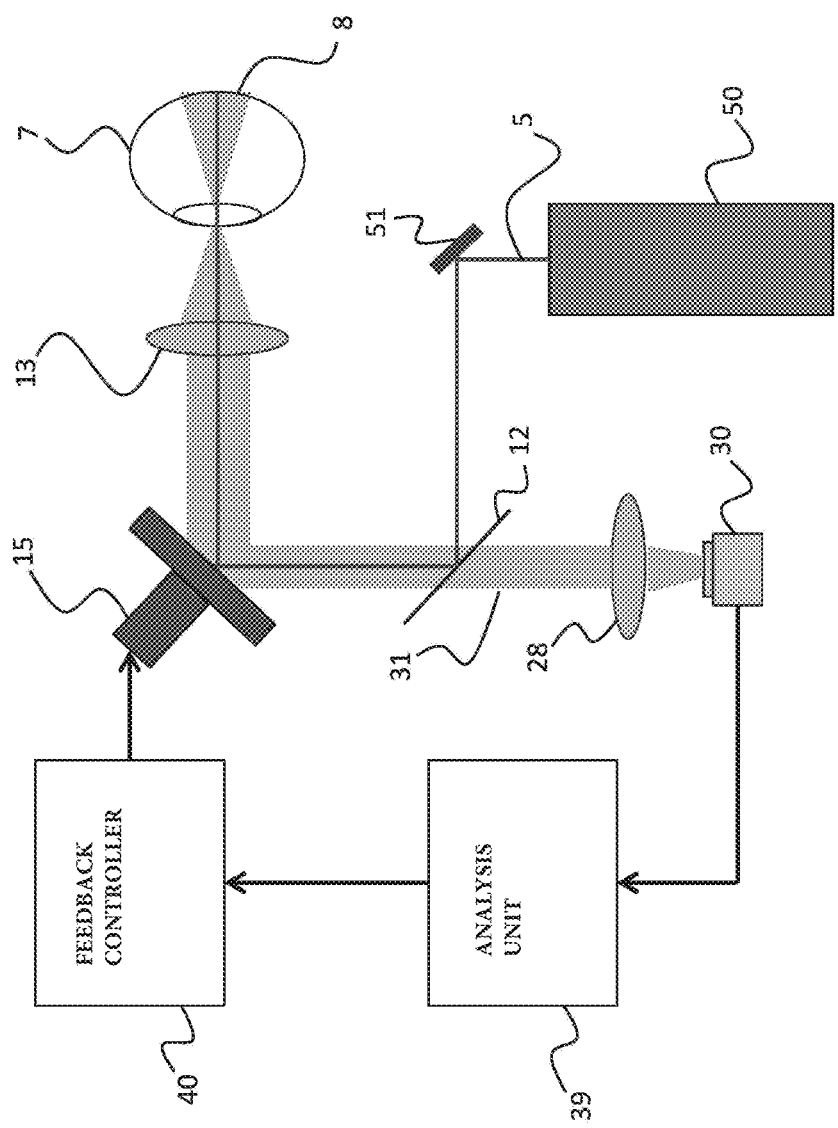
FIG. 3 schematically illustrates an optical coherent tomography system in accordance with yet a further embodiment of the present invention.

In the embodiments of FIGS. 1 and 2 each correction unit is illustrated comprising two galvanometer coupled mirrors which allow correction of the direction in the x and y direction (i.e. perpendicular to the optical path). In the further embodiment of the invention illustrated in FIG. 3, a single optical correction unit 15 enables to correct both the field of view 31 of the tracking camera 30 as well as the beam 5 of imaging radiation provided by the OCT apparatus 50 to be corrected in both the x and y direction (perpendicular to the optical path). FIG. 3 further illustrates the beam 5 impinging on the fundus 8 of eye 7, as well as the schematic imaging area on fundus 8 for the tracking image. Scanning of the beam 5 across the examination area may be performed by actuating the mirror 51 in the optical path of the beam 5.

Figure 4:
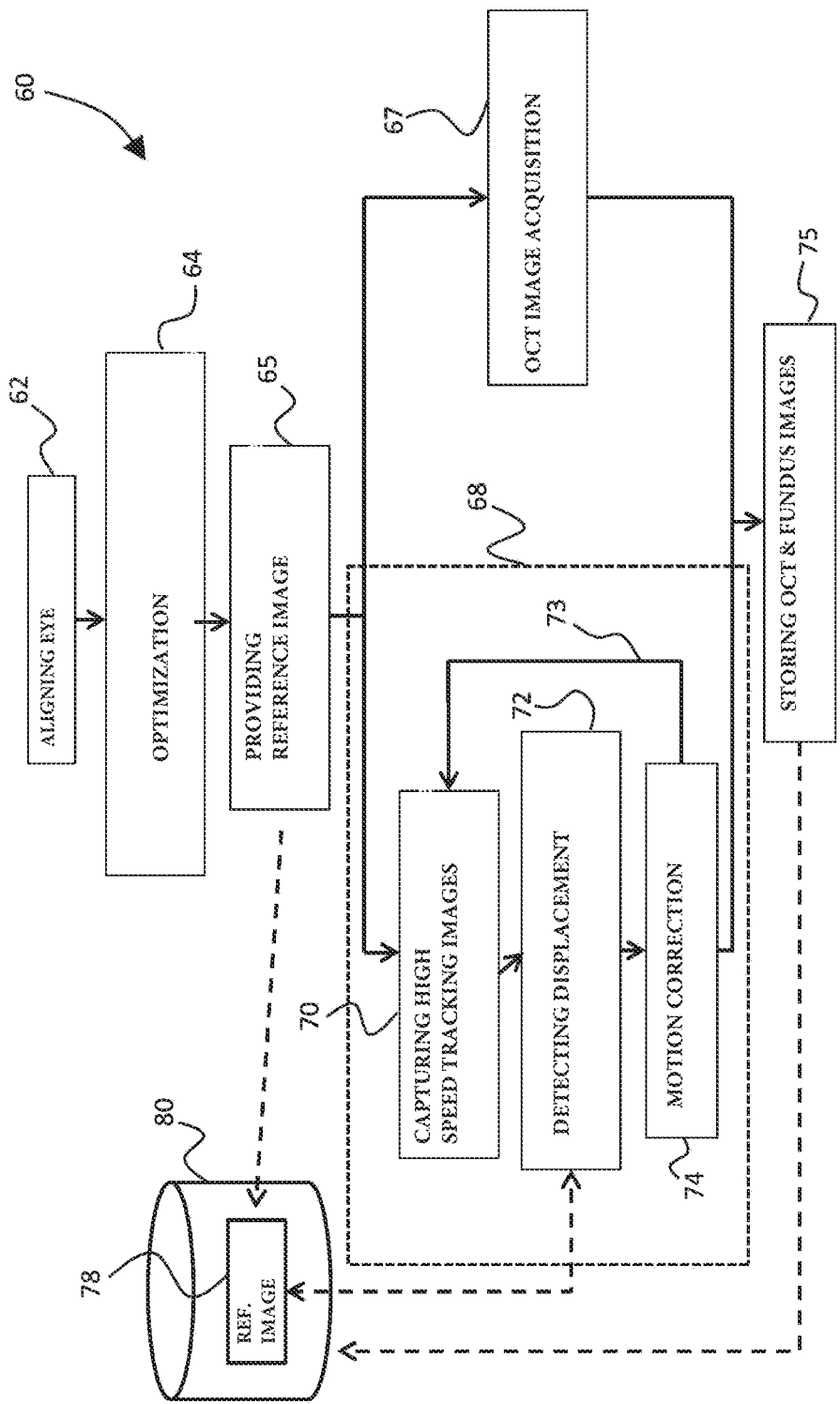
FIG. 4 illustrates a method in accordance with the present invention.

FIG. 4 schematically illustrates an optical coherent tomography method in accordance with an embodiment of the present invention. The method 60 includes a first step 62 of aligning the eye 7 with the field of view of the tracking camera 30, such as to set up the system before imaging of the fundus of the eye 7. The fundus image obtained with a tracking camera 30 is optimized in step 64 by focusing at the retina of the eye 7, and for example by moving to a location on the fundus having a high contrast. This for example may be the optical disc on the retina, but may likewise include veins or arteries, or any other structures providing a sufficient contrast on the surface of the fundus. Steps 62 and 64 together form the initialization of the system: setting up the system for performing the OCT imaging.

As will be appreciated, to enable accurate detection of displacement due to eye movements, a high enough signal to noise ratio (SNR) is required. At the same time, however, a high imaging rate of the tracking camera is desired such as to make the magnitude of the displacements between subsequent images of the tracking camera as small as possible. Small displacements detected at a high imaging rate enable to closely follow the movements of the eye with the tracking camera 30 as well as with the OCT beam 5. However, increasing the imaging rate of the tracking camera automatically reduces the maximum exposure time that can be used for obtaining each of the subsequent tracking images. A shorter exposure time reduces the signal-to-noise ratio (SNR), thereby complicating the detection of the displacements. In accordance with the present invention, by correcting the field of view of the camera in addition to correcting of the direction of the beam of imaging radiation, the size of the tracking images can be reduced. As a result, the processing of the subsequent tracking images can be performed faster, which allows more exposure time per tracking image to be available. Therefore, the reduction of the size of the tracking images already at least partly makes up for the higher imaging rate and decreased exposure time.

As a further improvement to the optical coherent tomography method of the present invention, the method further includes a step of providing a reference tracking image (step 65). This reference image is obtained in step 65 in FIG. 4 prior to obtaining the subsequent tracking images in branch 68 of the method of FIG. 4. In step 65, a reference image is obtained using a long or at least long enough exposure time. The reference image therefore comprises a high signal-to-noise ratio and reveals many details on the fundus of the eye. As will be illustrated further below with reference to FIGS. 7A-7C, the use of a reference image obtained with a long enough exposure time greatly reduces inaccuracies in the detection of displacements due to eye movement. As a result, the use of a reference image with long exposure time (e.g. 10 milliseconds) and/or high illumination power (e.g. 10 milliwatt) enables to further reduce the exposure time of the subsequent tracking images such as to obtain a high imaging rate for the tracking camera.

After obtaining the reference tracking image in step 65, the actual OCT imaging starts by performing the OCT image acquisition using the beam of imaging radiation in step 67, while at the same time in a simultaneous process performing the tracking in branch 68 of the process. The tracking includes the capturing of high speed tracking images in step 70. The high speed tracking images are obtained using a short exposure time, e.g. smaller than 1 millisecond. Using the reference image 78 which is stored in memory 80 of the system, in step 72 the displacement of the fundus is detected based on the obtained tracking image in step 70, and the preceding tracking image obtained before. To enable detection of the displacement, a correlation is made between the highly detailed reference image 78, and the tracking image (and its preceding image) obtained in step 70. Then, when the displacement caused by eye movement has been accurately detected, motion correction is applied in step 74. In accordance with the present invention this motion correction is applied both on the field of view 31 of the tracking camera 30 as well as on the beam 5 of imaging radiation of the OCT apparatus. For the duration of the OCT imaging in step 67, the tracking in branch 68 of the method is continued, as is illustrated by arrow 73. Therefore, as long as the OCT imaging is being performed, new tracking images are obtained in step 70 and analyzed in step 72 for detecting any displacement. When the OCT imaging has been completed, tracking is no longer required and the method continues in step 75 where both the OCT image obtained in step 67 as well as the fundus image (or images) are stored in memory 80.

An alternative to the method disclosed in FIG. 4 is illustrated in FIG. 5. FIG. 5 starts with step 92 wherein the tracking camera 30 and the eye 7 are aligned, similar as in step 62 of FIG. 4. Next, in step 94, the initialization is performed by focusing at the retina and moving to a location with high contrast, such as the optical disc on the retina (like in step 64 of FIG. 4). In the embodiment of the method illustrated in FIG. 5, the step of obtaining a reference image having a long exposure time has been omitted, but is implemented in a different manner. The step of obtaining a reference image is in FIG. 5 not a separate step in the method. Instead, a reference image with desired exposure time is created using any number of subsequent tracking images obtained during tracking.

In FIG. 5, after initialization in step 94, the method continues with the actual OCT imaging process in step 96. Simultaneously, in steps 98-101, the tracking of the fundus and detection of any displacement caused by eye motion is performed in a manner similar to steps 70-74 of FIG. 4. Likewise, in step 98 (as in step 70) the tracking camera 30 captures high speed tracking images with a short exposure time, and stores these high speed tracking images 82 in memory 80. The memory 80 also comprises the (highly detailed) reference image 78 obtained with long exposure time in a manner to be explained further below. In step 99, displacement of the fundus of the eye 7 is detected by analyzing two subsequent high speed tracking images while correlating these high speed tracking images with the detailed reference image 78 from memory 80. As in step 74, motion correction of the field of view 31 of the tracking camera 30 and the beam 5 of the OCT apparatus is performed based on the detected displacement, and thereafter either a new tracking image is taken in step 98 as indicated by arrow 101, or (if step 96 has been completed) the tracking is discontinued and the method continues in step 112. In step 112, the OCT image obtained in step 96 is stored in memory 80.

During tracking in steps 98-101, as already referred to above, a reference image with high signal-to-noise ratio using long exposure time is created. The creation of this reference image is performed 'on the fly'. To this end, in step 105 a number of high speed tracking images 82 is retrieved from memory 80 while being stored therein from tracking camera 30. In step 107, the high speed images 82 are analyzed, and an area of overlap that is present in all of the analyzed images is determined. Where necessary, any high speed tracking images that do not have a large enough area of overlap with the other images, or for which the image quality is low, may be discarded from the analysis or may be used for improving only a part of the reference image. In step 108, the detailed reference image 78 is created based on the data in the area of overlap in the high speed tracking images 82 that were selected in step 107. A detailed reference image 78 is stored in memory 80 for use in step 99 for tracking. Optionally, as illustrated by arrow 110, the reference image 78 may be improved by including further tracking images 82 'on the fly', by continuing the process again in step 105. Alternatively, in case a reference image having a large enough SNR is obtained in step 108, this branch of the method may alternatively be discontinued after step 108.

The embodiment of the method in FIG. 5 is based on the insight that instead of taking a reference image with a high exposure time in a separate step as illustrated by step 65 of FIG. 4, the combination of data from many high speed images 82 having a low exposure time may together result in a reference image having a high exposure time (or the equivalent thereof). As a result, the quality of the reference image 68 will quickly improve while more and more tracking images 82 are being used for creation thereof.

An example tracking image of a fundus camera that can be used as tracking camera 30 is illustrated in FIG. 6 (image 120). In the image 120, structures such as veins on the fundus are visible having a large enough contrast such as to be detectable for displacement detection.

Figure 7A:
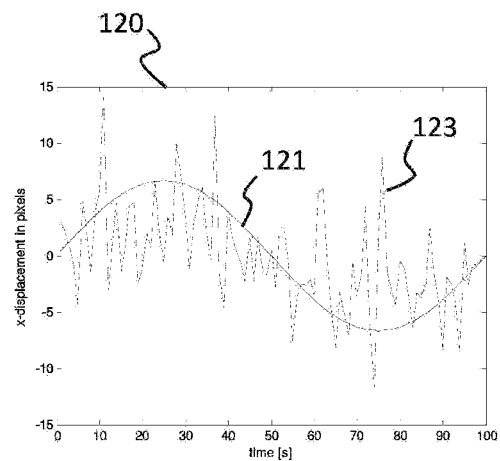
FIGS. 7A-7C illustrate simulated tracking results of displacement tracking.
Figure 7B:
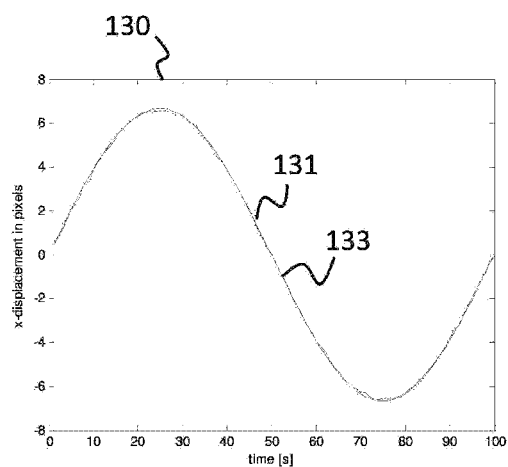
Figure 7C:
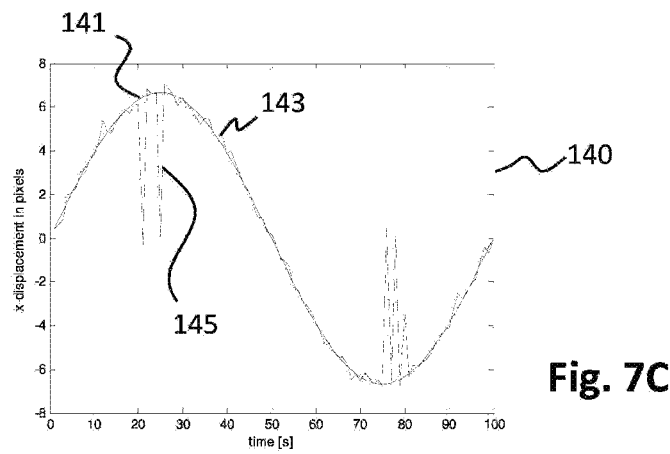

The results of a simulation which clearly indicate how tracking can be improved with the use of a clear reference image are illustrated in the graphs of FIGS. 7A-7C. In the simulation of FIGS. 7A-7C, a high contrast clean fundus image obtained using a fundus camera has been replicated to obtain a plurality of test images. Each test image was distorted with generated noise. Each of the test images comprises approximately 80% of noise (and 20% signal). Eye movement has been simulated throughout the test by imposing a displacement in the x direction on the test images over time. The displacement imposed is illustrated in FIG. 7A by the line 121. The imposed displacement of the images is thus exactly known. In the situation of FIG. 7A, the test images (with 80% noise) have been analyzed to predict the amount of displacement that was imposed. The result of this prediction is illustrated in FIG. 7A by the line 123 (from image to image). As follows from FIG. 7A, with 80% noise in the test images, the prediction method is not really able to accurately predict the amount of displacement imposed (i.e. line 121).

In FIG. 7B, the same prediction was repeated as in FIG. 7A, but including the use of the clean reference image. The clean reference image in the situation of FIG. 7B was actually the fundus image that was used to generate the test images, without the 80% noise distortion. During prediction of the displacement, each of the distorted images was first correlated with the clear reference image, and the displacement was determined after correlation with the reference image. In FIG. 7B, in the graph 130, line 131 is the imposed displacement on the test images. The predicted displacement is illustrated by line 133 in graph 130. As follows from FIG. 7B, using the clean reference image (with 0% added noise) and with correlation of the test images to the clean reference image, the imposed displacement can be accurately predicted from the test images, showing the potential of this method.

To simulate the use of a reference image in a real case, the same procedure as in FIG. 7B has been repeated in the situation of FIG. 7C. However, instead of using a clean reference image with 0% noise, the reference image that was used in the simulation of FIG. 7C included 10% added noise, which is realistic in case a real reference image with sufficient long exposure would be used. In FIG. 7C, the imposed displacement is illustrated by line 141. The predicted displacement is indicated by line 143. The predicted displacement 143 nicely follows the imposed displacement 141 with the exception of some occasional peaks 145 where the displacement is incorrectly determined. However, as follows from the results of FIG. 7C, the measurement errors in the predicted displacement may be easily filtered from the predicted results, for example using a low pass filter, or by fitting, or by any other suitable filtering technique. FIG. 7C proves that in a real life case, tracking images with a very short exposure time having a low signal-to-noise ratio (in the simulated case the SNR=0.2/0.8=0.25) may be correlated with a clear reference image having a sufficient signal-to-noise ratio (in the simulated situation SNR=0.9/0.1=9.0) to enable accurate detection of the displacement of the eye. Therefore, the use of a clear reference image with a low amount of noise can be used to reduce the exposure time of the subsequent tracking images. As a result, the imaging rate of the tracking camera can be increased such as to accurately follow the displacement.

The present invention is not exclusively applicable to optical coherence tomography, although this imaging technique has been used as an exemplary retinal imaging technique to explain the application and advantages of the invention. Alternatively, embodiments of the invention may include confocal scanning laser ophthalmology wherein a fundus of an eye is scanned step-by-step by a laser to obtain image data pixel-by-pixel. In that case, e.g. in the embodiment illustrated in FIG. 1, interferometry will not be applied and thus the mirror 21 in FIG. 1 may be absent or replaced by non-reflective element. Moreover, the beam received by optical sensor 23 will comprise the reflected radiation, and is analyzed by analysis unit 25 to provide the cSLO image. If, in accordance with a further embodiment, the applied optical retinal imaging technique relates to line scanning laser ophthalmology, additional optics may be present between radiation source 3 and beam splitter 9 to shape the beam 5 such as to provide a line-shaped scanning beam. In FIG. 3, the OCT apparatus 50 may be replaced by, or include, a cSLO or lSLO apparatus.

The present invention has been described in terms of some specific embodiments thereof. It will be appreciated that the embodiments shown in the drawings and described herein are intended for illustrated purposes only and are not by any manner or means intended to be restrictive on the invention. It is believed that the operation and construction of the present invention will be apparent from the foregoing description and drawings appended thereto. It will be clear to the skilled person that the invention is not limited to any embodiment herein described and that modifications are possible which should be considered within the scope of the appended claims. Also kinematic inversions are considered inherently disclosed and to be within the scope of the invention. In the claims, any reference signs shall not be construed as limiting the claim. The term 'comprising' and 'including' when used in this description or the appended claims should not be construed in an exclusive or exhaustive sense but rather in an inclusive sense. Thus the expression 'comprising' as used herein does not exclude the presence of other elements or steps in addition to those listed in any claim. Furthermore, the words 'a' and 'an' shall not be construed as limited to 'only one', but instead are used to mean 'at least one', and do not exclude a plurality. Features that are not specifically or explicitly described or claimed may be additionally included in the structure of the invention within its scope. Expressions such as: "means for . . ." should be read as: "component configured for . . . " or "member constructed to . . . " and should be construed to include equivalents for the structures disclosed. The use of expressions like: "critical", "preferred", "especially preferred" etc. is not intended to limit the invention. Additions, deletions, and modifications within the purview of the skilled person may generally be made without departing from the spirit and scope of the invention, as is determined by the claims. The invention may be practiced otherwise then as specifically described herein, and is only limited by the appended claims.

The invention claimed is:

1. Optical retinal imaging method, comprising:
providing a beam of imaging radiation from a radiation source of an optical retinal imaging apparatus; directing, using directing optics, the beam of imaging radiation towards a fundus of a human or animal eye; and receiving a reflected portion of the imaging radiation by the optical retinal imaging apparatus;
wherein the method further comprises:
providing, by a tracking camera, a plurality of subsequent tracking images wherein each of the tracking images is obtained by the tracking camera at once within an exposure time, the tracking images including an image area covering at least a part of said fundus;
analyzing each of the tracking images by comparing with one or more earlier images for detecting a displacement of the fundus; and
adapting, at least dependent on the detected displacement, a direction of the beam of imaging radiation by actuating an optical corrector of said direction optics; and
in addition to said adapting of the direction of the beam of imaging radiation, adapting a location of the image area on said fundus imaged by the tracking camera at least dependent on the detected displacement.

2. Optical retinal imaging method according to claim 1, wherein said adapting of the location of the image area on the fundus is achieved by disposing the tracking camera such as to receive an optical tracking signal of said image area by the tracking camera via the optical corrector.

3. Optical retinal imaging method according to claim 1, further including a step of providing a reference tracking image, wherein the reference tracking image is obtained using an exposure time longer than an exposure time used for the subsequent tracking images.

4. Optical retinal imaging method according to claim 3, wherein said step of providing a reference tracking image is performed either by:
obtaining the reference tracking image as a separate step performed prior to the steps of subsequently providing the subsequent tracking images; or
obtaining the reference tracking image by combining image data from two or more of said subsequent tracking images such as to establish the longer exposure time of the reference tracking image.

5. Optical retinal imaging method according to claim 1, wherein the tracking camera is a fundus camera.

6. Optical retinal imaging method according to claim 1, wherein the optical retinal imaging method is at least one of a group comprising: an optical coherence tomography method, a confocal scanning laser ophthalmoscopy method, or a line scanning laser ophthalmoscopy method.

7. Optical retinal imaging method according to claim 1, wherein said adapting of the location of the image area on the fundus is achieved by disposing the tracking camera such as to receive an optical tracking signal of said image area by the tracking camera via the optical corrector, further including a step of providing a reference tracking image, wherein the reference tracking image is obtained using an exposure time longer than an exposure time used for the subsequent tracking images.

8. Optical retinal imaging method according to claim 7, wherein said step of providing a reference tracking image is performed either by:
obtaining the reference tracking image as a separate step performed prior to the steps of subsequently providing the subsequent tracking images; or
obtaining the reference tracking image by combining image data from two or more of said subsequent tracking images such as to establish the longer exposure time of the reference tracking image.

9. Optical retinal imaging system, comprising
an optical retinal imaging apparatus including a radiation source for providing a beam of imaging radiation, an optical receiver for receiving a reflected portion of the imaging radiation, and an analyzer for analyzing the received reflected portion of the imaging radiation;
the optical retinal imaging system further comprising
directing optics for directing the beam of imaging radiation towards a fundus of a human or animal eye, a tracking camera for providing a plurality of subsequent tracking images wherein each tracking image is obtained by the tracking camera at once within an exposure time, the tracking images including an image area covering at least a part of said fundus, and a controller for receiving the tracking images and analyzing each tracking image by comparing with one or more earlier images for detecting a displacement of the fundus during irradiation thereof by the optical retinal imaging apparatus;
wherein the directing optics include:
an optical corrector operatively connected to the controller for enabling adapting of a direction of the beam of imaging radiation at least dependent on the detected displacement, by actuation of the optical corrector; and
a camera image corrector for adapting, in addition to said adapting of the direction of the beam of imaging radiation, a location of the image area on said fundus imaged by the tracking camera at least dependent on the detected displacement.

10. Optical retinal imaging system according to claim 9, wherein the camera image corrector comprises the optical corrector.

11. Optical retinal imaging system according to claim 9, wherein the tracking camera is a fundus camera.

12. Optical retinal imaging system according to claim 9, wherein the optical corrector comprises at least one mirror connected to an actuator for controlling at least one of the orientation or position of the mirror relative to the beam of imaging radiation for adapting the direction thereof.

13. Optical retinal imaging system according to claim 9, further comprising a scanner for enabling scanning of said beam of imaging radiation across the fundus.

14. Optical retinal imaging system according to claim 9, wherein the controller is further arranged for obtaining a reference tracking image, wherein the reference tracking image is obtained using an exposure time and/or illumination power larger than that used for the subsequent tracking images.

15. Optical retinal imaging system according to claim 14, wherein the controller is arranged for obtaining the reference tracking image by combining image data from two or more of said subsequent tracking images such as to establish the longer exposure time of the reference tracking image.

16. Optical retinal imaging system according to claim 9, wherein the optical retinal imaging system comprises at least one of a group comprising: an optical coherence tomography system, a confocal scanning laser ophthalmoscopy system, or a line scanning laser ophthalmoscopy system.

17. Optical retinal imaging system according to claim 9, wherein the tracking camera is disposed such as to receive an optical tracking signal of said image area by the tracking camera via the optical corrector.

18. Optical retinal imaging system according to claim 17, wherein the controller is arranged for receiving a plurality of subsequent tracking images during said providing of the beam of imaging radiation, wherein the controller is further arranged for obtaining a reference tracking image, wherein the reference tracking image is obtained using an exposure time and/or illumination power larger than that used for the subsequent tracking images.

19. Optical retinal imaging system according to claim 18, wherein the controller is arranged for obtaining the reference tracking image by combining image data from two or more of said subsequent tracking images such as to establish the longer exposure time of the reference tracking image.

20. A non-transitory computer readable medium comprising a computer program product comprising instructions that, when executed by an optical retinal imaging system causes the system to perform a method comprising:
controlling a radiation source of an optical retinal imaging apparatus comprised by the system to provide a beam of imaging radiation; and controlling directing optics to direct the beam of imaging radiation towards a fundus of a human or animal eye; and controlling the optical retinal imaging apparatus receive a reflected portion of the imaging radiation;

the method further comprises:

controlling a tracking camera to provide a plurality of subsequent tracking images wherein each of the tracking images is obtained by the tracking camera at once within an exposure time, the tracking images including an image area covering at least a part of said fundus; and obtaining and analyzing each of the tracking images by a controller by comparing with one or more earlier images for detecting a displacement of the fundus; and adapting, at least dependent on the detected displacement, a direction of the beam of imaging radiation by actuating an optical corrector of said direction optics; and in addition to said adapting of the direction of the beam of imaging radiation, adapting a location of the image area on said fundus imaged by the tracking camera at least dependent on the detected displacement.

\* \* \* \* \*